United States Patent
Leak et al.

(10) Patent No.: US 8,651,338 B2
(45) Date of Patent: Feb. 18, 2014

(54) DELIVERY OF TWO OR MORE MEDICAMENTS THROUGH A SINGLE DOSE SELECTION AND SINGLE DISPENSE INTERFACE

(75) Inventors: David Martin Leak, Lake Hopatcong, NJ (US); Malcolm Stanley Boyd, Wellesbourne (GB); David Aubrey Plumptre, Droitwich Spa (GB); Daniel Thomas De Sausmarez Lintell, Rugby (GB); Elizabeth Anne Marshall, Leamington Spa (GB); Christopher Smith, Holmes Chapel (GB); Elliot Lucas Ortiz, San Francisco, CA (US)

(73) Assignee: Sanofi-Aventis Deutschland GmbH, Frankfurt am Main (DE)

( * ) Notice: Subject to any disclaimer, the term of this patent is extended or adjusted under 35 U.S.C. 154(b) by 0 days.

(21) Appl. No.: 13/375,679

(22) PCT Filed: Jun. 1, 2010

(86) PCT No.: PCT/EP2010/057574
§ 371 (c)(1),
(2), (4) Date: Feb. 8, 2012

(87) PCT Pub. No.: WO2010/139668
PCT Pub. Date: Dec. 9, 2010

(65) Prior Publication Data
US 2012/0125951 A1     May 24, 2012

Related U.S. Application Data

(60) Provisional application No. 61/183,464, filed on Jun. 2, 2009.

(30) Foreign Application Priority Data

Jul. 25, 2009   (EP) .................................. 09009658

(51) Int. Cl.
B65D 88/54    (2006.01)
G01F 11/00    (2006.01)
B67D 7/70     (2010.01)

(52) U.S. Cl.
USPC .......................................... 222/309; 222/137

(58) Field of Classification Search
USPC ................... 222/309, 137, 145.5, 145.6, 390; 604/187, 191, 207, 208, 211, 218
See application file for complete search history.

(56) References Cited

U.S. PATENT DOCUMENTS 3,767,085 A * 10/1973 Cannon et al. ................... 222/82
5,104,375 A *  4/1992 Wolf et al. ...................... 604/518

(Continued)

FOREIGN PATENT DOCUMENTS

WO         9403392 A1    2/1994
WO    WO 9403392 A1 *  2/1994

(Continued)

*Primary Examiner* — Paul R Durand
*Assistant Examiner* — Benjamin R Shaw
(74) *Attorney, Agent, or Firm* — McDonnell Boehnen Hulbert & Berghoff LLP

(57) ABSTRACT

A injection system for co-delivery of two medicaments (1, 2) having a drug delivery device (10) containing a primary reservoir containing a first medicament (1) and that has a secondary reservoir containing a second medicament (2) where the drug delivery device (10) has only one dose setter (12) for the primary reservoir and that automatically determines the dose of the second medicament (2). Both medicaments (1, 2) are delivered through a single dispense interface.

14 Claims, 1 Drawing Sheet

(56) References Cited

U.S. PATENT DOCUMENTS

| | | | |
|---|---|---|---|
| 6,540,113 B2 * | 4/2003 | Gardos | 222/137 |
| 6,564,972 B2 * | 5/2003 | Sawhney et al. | 222/137 |
| 7,748,980 B2 * | 7/2010 | Mulhauser et al. | 433/89 |
| 2002/0113088 A1 * | 8/2002 | Pierson et al. | 222/137 |
| 2004/0251274 A1 * | 12/2004 | Ponton | 222/134 |
| 2010/0282774 A1 * | 11/2010 | Greter et al. | 222/39 |
| 2012/0043347 A1 * | 2/2012 | Meron et al. | 222/137 |
| 2012/0148980 A1 * | 6/2012 | Gramann | 433/90 |

FOREIGN PATENT DOCUMENTS

| | | |
|---|---|---|
| WO | 9632973 A1 | 10/1996 |
| WO | WO 9632973 A1 * | 10/1996 |
| WO | 2008119691 A2 | 10/2008 |
| WO | WO 2008119691 A2 * | 10/2008 |

* cited by examiner

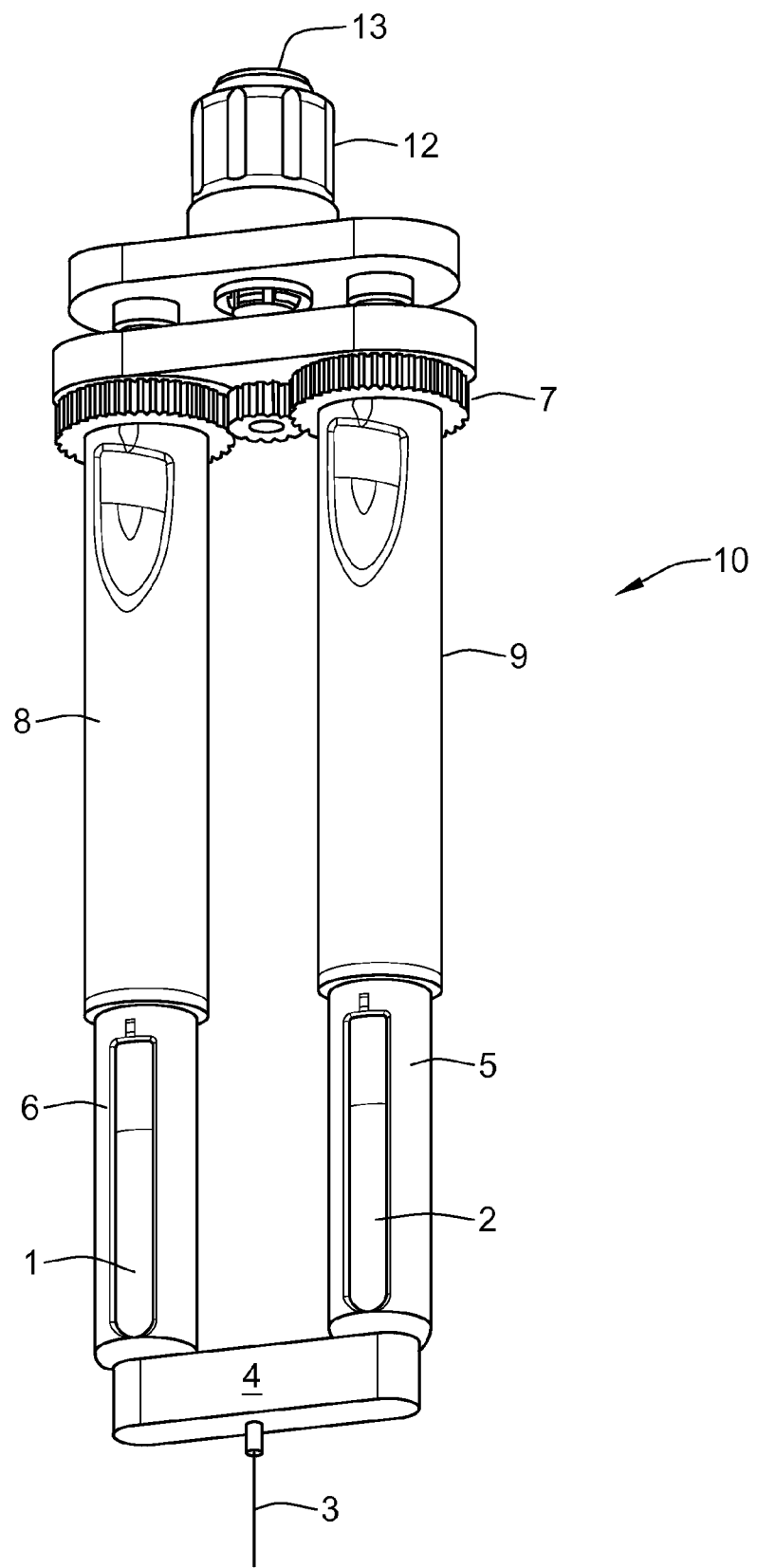

DELIVERY OF TWO OR MORE MEDICAMENTS THROUGH A SINGLE DOSE SELECTION AND SINGLE DISPENSE INTERFACE

CROSS REFERENCE TO RELATED APPLICATIONS

The present application is a 35 U.S.C. 371 National Application of PCT/EP2010/057574 filed Jun. 1, 2010, which claims priority to U.S. Provisional Patent Application No. 61/183,464 filed Jun. 2, 2009 and European Patent Application No. 09009658.7 filed Jul. 25, 2009, the entire contents of which are incorporated entirely herein by reference.

FIELD OF THE PRESENT APPLICATION

According to specific embodiments, this disclosure relates to medical devices and methods of delivering at least two drug agents from separate reservoirs using devices having only a single dose setter and a single dispense interface. In specific embodiments, a single delivery procedure initiated by the user causes a non-user settable dose of a second drug agent and a user-variable set dose of a first drug agent to be delivered to the patient. The drug agents are contained in two or more multiple dose reservoirs, containers or packages, each containing independent (single drug compound) or pre-mixed (co-formulated multiple drug compounds) drug agents. Our invention may be of particular benefit where the therapeutic response can be optimized for a specific target patient group, through control and definition of the therapeutic profile.

BACKGROUND

Certain disease states require treatment using one or more different medicaments. Some drug compounds need to be delivered in a specific relationship with each other in order to deliver the optimum therapeutic dose. Here, combination therapy may be desirable, but not possible in a single formulation for reasons such as, but not limited to, stability, compromised therapeutic performance and toxicology.

For example, in some cases it might be beneficial to treat a diabetic with a long acting insulin and with a glucagon-like peptide-1 (GLP-1), which is derived from the transcription product of the proglucagon gene. GLP-1 is found in the body and is secreted by the intestinal L cell as a gut hormone. GLP-1 possesses several physiological properties that make it (and its analogs) a subject of intensive investigation as a potential treatment of diabetes mellitus.

There are a number of potential problems when delivering two active medicaments or "agents" simultaneously. The two active agents may interact with each other during the long-term, shelf life storage of the formulation. Therefore, it is advantageous to store the active components separately and only combine them at the point of delivery, e.g. injection, needle-less injection, pumps, or inhalation. However, the process for combining the two agents needs to be simple and convenient for the user to perform reliably, repeatedly and safely.

A further problem is that the quantities and/or proportions of each active agent making up the combination therapy may need to be varied for each user or at different stages of their therapy. For example, one or more actives may require a titration period to gradually introduce a patient to a "maintenance" dose. A further example would be if one active requires a non-adjustable fixed dose while the other is varied in response to a patient's symptoms or physical condition. This problem means that pre-mixed formulations of multiple active agents may not be suitable as these pre-mixed formulations would have a fixed ratio of the active components, which could not be varied by the healthcare professional or user.

Additional problems arise where a multi-drug compound therapy is required, because many users cannot cope with having to use more than one drug delivery system or make the necessary accurate calculation of the required dose combination. This is especially true for users with dexterity or computational difficulties.

Accordingly, there exists a strong need to provide devices and methods for the delivery of two or more medicaments in a single injection or delivery step that is simple for the user to perform. In specific embodiments, our invention overcomes the above-mentioned problems by providing separate storage containers for two or more active drug agents that are then only combined and/or delivered to the patient during a single delivery procedure. Setting a dose of one medicament automatically fixes or determines the dose of the second medicament (i.e. non-user settable). Moreover, in specific embodiments, our invention also gives the opportunity for varying the quantity of one or both medicaments. For example, one fluid quantity can be varied by changing the properties of the injection device (e.g. dialing a user variable dose or changing the device's "fixed" dose). The second fluid quantity can be changed by manufacturing a variety of secondary drug containing packages with each variant containing a different volume and/or concentration of the second active agent. The user or healthcare professional would then select the most appropriate secondary package or series or combination of series of different packages for a particular treatment regime.

These and other advantages will become evident from the following more detailed description of the invention.

PROBLEM TO BE SOLVED

The general problem to be solved by the present invention is to provide a drug delivery system and a method where an administration of at least two medicaments is facilitated.

SUMMARY

In specific embodiments, our invention allows complex combination of multiple drug compounds within a single device. In particular a user may be enabled to set and dispense a multi-drug compound device through one single dose setting mechanism and a single dispense interface. This single dose setter may control the mechanism of the device such that a predefined combination of the individual drug compounds is delivered when a single dose of one of the medicaments is set and dispensed through the single dispense interface. Although principally described in this application as an injection device, the basic principle could be applicable to other forms of drug delivery, such as, but not limited to, inhalation, nasal, ophthalmic, oral, topical, and like devices.

By defining the therapeutic relationship between the individual drug compounds, our delivery device may help ensure that a patient/user receives the optimum therapeutic combination dose from a multi-drug compound device without the inherent risks associated with multiple inputs, where the user has to calculate and set the correct dose combination every time they use the device. The medicaments can be fluids, defined herein as liquids, gases or powders that are capable of flowing and that change shape at a steady rate when acted upon by a force tending to change its shape. Alternatively, one of the medicaments may be a solid that is carried, solubilized or otherwise dispensed with another fluid medicament.

The disclosed drug delivery device may be of particular benefit to users with dexterity or computational difficulties as the single input and associated predefined therapeutic profile may remove the need for them to calculate their prescribed dose every time they use the device and the single input may allow considerably easier setting and dispensing of the combined compounds.

In a preferred embodiment a master drug compound, such as insulin, contained within a multiple dose, user selectable device could be used with a single use, user replaceable, module that contains a single dose of a secondary medicament and the single dispense interface. When connected to the primary device the secondary compound is activated/delivered on dispense of the primary compound. Although our invention specifically mentions insulin, insulin analogs or insulin derivatives, and GLP-1 or GLP-1 analogs as two possible drug combinations, other drugs or drug combinations, such as an analgesics, hormones, beta agonists or corticosteroids, or a combination of any of the above-mentioned drugs could be used with our invention.

For the purposes of our invention the term "insulin" shall mean Insulin, insulin analogs, insulin derivatives or mixtures thereof, including human insulin or a human insulin analogs or derivatives. Examples of insulin analogs are, without limitation, Gly(A21), Arg(B31), Arg(B32) human insulin; Lys (B3), Glu(B29) human insulin; Lys(B28), Pro(B29) human insulin; Asp(B28) human insulin; human insulin, wherein proline in position B28 is replaced by Asp, Lys, Leu, Val or Ala and wherein in position B29 Lys may be replaced by Pro; Ala(B26) human insulin; Des(B28-B30) human insulin; Des (B27) human insulin or Des(B30) human insulin. Examples of insulin derivatives are, without limitation, B29-N-myristoyl-des(B30) human insulin; B29-N-palmitoyl-des(B30) human insulin; B29-N-myristoyl human insulin; B29-N-palmitoyl human insulin; B28-N-myristoyl LysB28ProB29 human insulin; B28-N-palmitoyl-LysB28ProB29 human insulin; B30-N-myristoyl-ThrB29LysB30 human insulin; B30-N-palmitoyl-ThrB29LysB30 human insulin; B29-N—(N-palmitoyl-Y-glutamyl)-des(B30) human insulin; B29-N-(N-lithocholyl-Y-glutamyl)-des(B30) human insulin; B29-N-(ω-carboxyheptadecanoyl)-des(B30) human insulin and B29-N-(ω-carboxyheptadecanoyl) human insulin.

As used herein the term "GLP-1" shall mean GLP-1, GLP-1 analogs, or mixtures thereof, including without limitation, exenatide (Exendin-4(1-39), a peptide of the sequence H-His-Gly-Glu-Gly-Thr-Phe-Thr-Ser-Asp-Leu-Ser-Lys-Gln-Met-Glu-Glu-Glu-Ala-Val-Arg-Leu-Phe-Ile-Glu-Trp-Leu-Lys-Asn-Gly-Gly-Pro-Ser-Ser-Gly-Ala-Pro-Pro-Pro-Ser-NH$_2$), Exendin-3, Liraglutide, or AVE0010 (H-His-Gly-Glu-Gly-Thr-Phe-Thr-Ser-Asp-Leu-Ser-Lys-Gln-Met-Glu-Glu-Glu-Ala-Val-Arg-Leu-Phe-Ile-Glu-Trp-Leu-Lys-Asn-Gly-Gly-Pro-Ser-Ser-Gly-Ala-Pro-Pro-Ser-Lys-Lys-Lys-Lys-Lys-Lys-NH$_2$).

Examples of beta agonists are, without limitation, salbutamol, levosalbutamol, terbutaline, pirbuterol, procaterol, metaproterenol, fenoterol, bitolterol mesylate, salmeterol, formoterol, bambuterol, clenbuterol, indacaterol.

Hormones are for example hypophysis hormones or hypothalamus hormones or regulatory active peptides and their antagonists, such as Gonadotropine (Follitropin, Lutropin, Choriongonadotropin, Menotropin), Somatropine (Somatropin), Desmopressin, Terlipressin, Gonadorelin, Triptorelin, Leuprorelin, Buserelin, Nafarelin, Goserelin.

One embodiment of our invention relates to a drug delivery system to deliver two or more medicaments through a dose setter, preferably a single dose setter, and a single dispense interface where the device has a housing containing a user-operable dose setter operably connected to a primary reservoir of a first medicament containing one or more doses of at least one drug agent. The primary reservoir may contain multiple doses of at least one drug agent. A dose button is operably connected to the primary reservoir of medicament and a single dispense interface is configured for fluid communication with the primary reservoir. A secondary reservoir of a second medicament containing one or more doses of at least one drug agent is configured for fluid communication to the single dispense interface. The secondary reservoir may contain multiple doses of at least one drug agent. A single activation of the dose setter by a user sets a dose from the primary reservoir and automatically sets a dose of the second medicament. In particular, the second medicament may be not user-settable. Here, the device may comprise only a single user-operable dose setter. A single activation of the dose button causes the set dose of the first medicament from the primary reservoir and the automatically set dose of the second medicament to be expelled through the single dispense interface. In particular, the device may comprise a first and a second dispense mechanism, wherein on activation of the dose button the first dispense mechanism causes the dose of the first medicament to be forced through the dispense interface and the second dispense mechanism causes the dose of the second medicament to be forced through the dispense interface.

This dose button can be any type of mechanism that triggers the delivery procedure, whether driven mechanically or through a combination of electronics and mechanics. The button can move or be a touch sensitive virtual button, for example, a touch sensitive screen. Our drug delivery system has a single dispense interface configured for fluid communication with the primary reservoir and with a secondary reservoir of medicament containing at least one drug agent. The single dispense interface can be any type of outlet that allows the two or more medicaments to exit the drug delivery system and be delivered to the patient. Types of interfaces include hollow needles, catheters, atomizers, pneumatic injectors, or needle-less injectors, mouthpieces, nasal-applicators and the like interfaces. The single dispense interface also may comprise a system of hollow needle cannulae configured for fluid communication with the primary reservoir and with a secondary reservoir of medicament containing at least one drug agent. For example the system of hollow needle cannulae may comprise a first needle in fluid communication with the primary reservoir, a second needle in fluid communication with the secondary reservoir, and an output needle (3) operably connected to enable fluid communication with both the first and the second needle, i.e. wherein the system of hollow needle cannulae is in fluid communication with the primary and secondary reservoirs.

The secondary reservoir may contain multiple doses of medicament. The system is designed such that a single activation of the dose button causes the user set dose of medicament from the primary reservoir and a non-user set dose of medicament from the second reservoir to be expelled through the single dispense interface. By user settable dose it is meant dose that the user (patient or health care provider) can physically manipulate the device to set a desired dose. Additionally, the user settable dose can be set remotely through the use of wireless communication (Bluetooth, WiFi, satellite, etc.) or the dose could be set by another integrated device, such as a blood glucose monitor after performing a therapeutic treatment algorithm. By non-user set dose it is meant that the user (or any other input) cannot independently set or select a dose of medicament from the secondary reservoir. In other words, when the user (or another input as described above) sets the dose of the primary medicament in the primary reservoir, the dose of the second medicament is automatically set.

Our disclosure also covers a method of dispensing a variable of one medicament and a fixed dose of a second medicament from separate reservoirs that involves the steps of first setting a dose of a first medicament contained in a primary reservoir of a drug delivery device optionally having a single dose setter. Moreover, a method of dispensing a user settable dose of a primary medicament and a dose of a second medicament from separate reservoirs is disclosed that involves the steps of first setting a dose of a first medicament contained in a primary reservoir of a drug delivery device. The dose may be set by operating a single dose setter. This setting of the first dose automatically sets the dose from a secondary reservoir based on the set dose of the first medicament. Preferably, this setting is effected without a separate input by the user. Next a dose button is activated that moves both the set dose of the first medicament from the primary reservoir and the automatically set dose from the secondary reservoir through a single dispense interface. Here, the first and second medicament is moved in a distal direction and forced through the single drug dispense interface.

The combination of compounds as discrete units or as a mixed unit can be delivered to the body via an integral needle. This would provide a combination drug injection system that, from a user's perspective, would be achieved in a manner that very closely matches the currently available injection devices that use standard needles. One possible delivery procedure would involve the following steps:

1. Attach a single dispense interface, such as a needle hub, to the distal end of the injection device such that the proximal end of the single dispense interface is in fluidic communication with both the primary compound and secondary compound.
2. Dial up/set the injection device such that it is ready to dispense the desired dose of the primary compound. As the single dose setter sets the dose of the primary compound, a predefined non-user settable dose of the secondary compound is automatically set at the same time.
3. Insert or apply the distal end of the single dispense interface to the patient at or into the desired administration site. Dose the primary compound by activating a single dose button, which also causes the secondary compound to automatically dispense.

The drug delivery system of our invention is preferably designed in such a way as to limit its use to exclusive primary and secondary reservoirs through employment of dedicated or coded features. In some situations it may be beneficial from a therapeutic and safety point of view to ensure that the primary reservoir can be a standard drug containing vial or cartridge. This would allow the user to deliver a combined therapy when a secondary reservoir is included in the device, but would also allow delivery of the primary compound independently through a standard drug dispense interface in situations, such as, but not limited to, dose splitting (i.e. delivering the complete dose of the primary therapy in two separate injections) or top-up of the primary compound in a way that would prevent the potential risk of double dosing of the secondary compound.

A particular benefit of specific embodiments of our invention is that the use of two multi-dose reservoirs makes it possible to tailor dose regimes when required, especially where a titration period is necessary for a particular drug. The secondary reservoir could be supplied in a number of titration levels with obvious differentiation features such as, but not limited to, aesthetic design of features or graphics, numbering etc, so that a user could be instructed to use the supplied secondary reservoirs in a specific order to facilitate titration. Alternatively, the prescribing physician may provide the patient with a number of "level one" titration secondary reservoirs and then when these were finished, the physician could then prescribe the next level. A key advantage of this titration program is that the primary device remains constant throughout.

In a preferred embodiment of our invention, the drug delivery device is used more than once and therefore is multi-use. Such a device may or may not have a replaceable reservoir of the primary drug compound, but our invention is equally applicable to both scenarios. It is possible to have a suite of different secondary reservoirs for various conditions that could be prescribed as one-off extra medication to patients already using a standard drug delivery device. Should the user attempt to reuse an empty secondary reservoir, our invention could include features that could alert the user to this situation. Such means of alerting the user may include some (or all) of the following:

1. Physical prevention of secondary reservoir re-attachment to the drug delivery device once the module has been used and removed.
2. Physical prevention of re-use of the used drug dispense interface by the user (e.g. a single use needle-guard type arrangement).
3. Physical/hydraulic prevention of subsequent liquid flow through the drug dispense interface once it has been used.
4. Physical locking of the dose setter and/or dose button of the drug delivery device.
5. Visual warnings (e.g. change in color and/or warning text/indicia within an indication window on the device or reservoirs once insertion and/or fluid flow has occurred).
6. Tactile feedback (presence or absence of tactile features on the outer surface of the device or dispense interface following use).

A further feature of the preferred embodiment may be that both medicaments are delivered via one injection needle and in one injection step. This offers a convenient benefit to the user in terms of reduced user steps compared to administering two separate injections. This convenience benefit may also result in improved compliance with the prescribed therapy, particularly for users who find injections unpleasant, or who have dexterity or computational difficulties. The use of one injection instead of two reduces the possibility for user errors and so may increase patient safety.

According to specific embodiments, our invention also covers a method of delivering two medicaments stored in separate primary packages. The medicaments may both be liquid, or alternatively one or more of the medicaments may be a powder, suspension or slurry. In one embodiment the secondary reservoir could be filled with a powdered medicament that is either dissolved or entrained in another fluid before it is injected with the primary medicament through the single dispense interface.

As mentioned, in the broadest scope these medicaments could be delivered via a number of routes of administration, for example needle based injections (as described), needleless injection, inhalation etc. For example, an inhaler version of our invention could have the secondary reservoir containing a liquid, solid or gas form of the second medicament that connects to an MDI or DPI inhaler. The mouthpiece would be part of the single dispense interface. The user would inhale through the mouthpiece, actuating the MDI or DPI inhaler as normal. As the air and medicament passes through the secondary reservoir the second medicament would become entrained in the airflow and delivered to the patient.

These as well as other advantages of various aspects of the present invention will become apparent to those of ordinary skill in the art by reading the following detailed description, with appropriate reference to the accompanying drawings.

The scope of the invention is defined by the content of the claims. The invention is not limited to specific embodiments but comprises any combination of elements of different embodiments. Moreover, the invention comprises any combination of claims and any combination of features disclosed by the claims.

BRIEF DESCRIPTION OF THE DRAWINGS

Exemplary embodiments are described herein with reference to the drawing, in which:

FIG. 1 illustrates an embodiment of the drug delivery system of the present invention having two multi-dose reservoirs positioned side-by-side containing a primary medicament and a secondary medicament, respectively.

DETAILED DESCRIPTION

According to specific embodiments of the disclosed drug delivery device, a non-user settable or fixed or predetermined dose of a second medicament (secondary drug compound) and a variable dose of a first medicament (primary drug compound) through a single output or drug dispense interface is dispensed. Setting the dose of the primary medicament by the user automatically determines the fixed dose of the second medicament. In a preferred embodiment the drug dispense interface is a needle cannula (hollow needle). FIG. 1 illustrates one possible embodiment of our invention, where a multi-use injection device 10 (housing not shown) has two reservoirs that are positioned side-by-side with one containing a first medicament 1 and the other a second medicament 2. As an example, the first medicament 1 is insulin. The second medicament 2 may be a GLP 1. Preferably, these reservoirs contain multiple doses of each medicament. Each reservoir is preferably self-contained and provided as sealed and sterile cartridges. These cartridges can be of different volumes and replaceable when empty or they can be fixed (non-removable) in the system. They can also have pierceable seals or septa to accept needle cannula.

The cartridges are preferably housed in cartridge holders 5 and 6 that have attachment means compatible with a removable, disposable hub or housing 4 that contains the single dispense interface. In this preferred embodiment the single dispense interface is shown as output needle 3. The hub can be of any design, provided that it allows for fluid communication between the primary and secondary medicaments and the single dispense interface or needle 3. A preferred design of hub 4 would include what is referred to in the art as a "2-to-1 needle" configuration. Although not shown, hub 4 could be supplied by a manufacturer contained in a protective and sterile capsule or container where the user would peel or rip open a seal or the container itself to gain access to the sterile single dispense interface. In some instances it might be desirable to provide two or more seals for each end of the hub. The seal may allow display of information required by regulatory labeling requirements. When a needle is used to deliver the medicaments it is preferred that the hub is designed to be economical and safe for allowing the user to attach a new hub for each injection. Attachment of hub 4 to the multi-use device 10 creates a fluid connection between output needle 3 and medicaments 1 and 2.

The embodiment in FIG. 1 uses a rotational coupling 7 to mechanically link two dose delivery assemblies 8 and 9 in such a way that rotation of a single dose setter 12 allows the user to select a dose of the primary medicament 1 and automatically set a fixed or predetermined non-user settable dose of secondary medicament 2. In the preferred embodiment illustrated, the rotational coupling has been embodied as a gear train in which counter-clockwise rotation of the single dose setter causes clockwise rotation of dial components (not shown) within the dose delivery assemblies 8 and 9. The fact that both dial components rotate in the same direction (i.e. clockwise) is beneficial in that it allows both dose delivery assemblies to be of similar construction in terms of the direction of the helically threaded components and is also likely to be more intuitive for a user to understand. Preferably, rotational coupling 7 is constructed such that it moves vertically at the same rate as both of the dial components. This allows it to set and dispense both drug compounds throughout the full operational range of the device.

As well understood by those skilled in the art, it is convenient to use lead screws or piston rods to push on a piston or bung contained within a cartridge of medicament As such, it is preferred to use lead screws in each dose delivery assembly. Thereby, for each medicament, a separate dispense mechanism is provided. In a further embodiment at least one piston rod is rotatable. In a further embodiment at least one of the rotatable piston rods comprises two distinct threads.

By varying the lead screw pitches it is possible to vary the dose sizes (and dose ratio) in relation to each other. Specifically, this allows variation of the therapeutic profile to suit a specific therapy or patient requirements by providing devices with different dose ratios. The device shown in FIG. 1 could be operated as follows:

a. Counter-clockwise rotation of the dose setter 12 causes counter-clockwise rotation of the drive gear and clockwise rotation of both driven gears in rotational coupling 7. Clockwise rotation of both driven gears forces both dial components in dose delivery assemblies 8 and 9 to rotate in the same direction and follow a helical path out of the body of the device. This operation allows the user to set a target dose of medicament 1, but not medicament 2, which is automatically set by whatever dose is selected for medicament 1.

b. Initiation of the dosing phase begins with the actuation of dispense or dose button 13 by the user. This causes the dial components to rotate independently of the dose setter.

c. During the dosing phase, the direction of rotation of the single dose setter as well the internal components of both device mechanisms is reversed. The rotational coupling 7 moves back towards the body of the device as both dial components wind back into the mechanisms following their respective helical paths. This reversal of rotation of both mechanisms coupled with the internal overhauling of the lead screws by internal drive sleeves (not shown) causes both medicaments to be dispensed in a simultaneous fashion following the fixed ratio profile defined when the user set the target dose of medicament 1.

Varying the lead screw pitches of the individual device mechanisms in relation to each other may alter the relationship of the fixed ratio of medicaments. Variation of the lead screw pitch changes the advance of the lead screw during dispense for a given amount of rotation during setting. Differing amounts of advance between the two mechanisms has the effect of creating different dispense ratios between the mechanisms. Variation of the lead screw pitches may have the effect of extending the operational window of delivery device 10 in terms of the range of fixed ratios that can be achieved.

This may also assist in keeping the lead screw pitch in a range that allows resetting should the device be required to be reusable. This means that multiple pen injectors each having a different therapeutic profile can be manufactured. Specifically, this allows variation of the therapeutic profile to suit a specific titration regime and ultimately individual patient requirements.

The attachment means between hub 4 and cartridge holders 5 and 6 can be any known to those skilled in the art, including threads, snap locks, snap fits, luer locks, bayonet, snap rings, keyed slots, and combinations of such connections. The connection or attachment between the hub and the cartridge holder may also contain additional features (not shown), such as connectors, stops, splines, ribs, grooves, pips, clips and the like design features, that ensure that specific hubs are attachable only to matching drug delivery devices. Such additional features would prevent the insertion of a non-appropriate primary or secondary reservoir to a non-matching injection device.

The shape of the dispense device 10, including hub 4, may be generally oval and/or cylindrical or any other geometric shape suitable for hand manipulation by a user. Additionally, hub 4 could incorporate a safety shield device that would prevent accidental needle sticks and reduce the anxiety experienced by users who suffer from needle phobia. The exact design of the safety shield is not critical to our invention, however, a preferred design is one that is operably connected to the first and/or second reservoirs. In such a design the activation of the safety shield could unlock the drug delivery system or instigate fluid communication between the reservoirs and in some cases cause the second medicament to be dispensed prior to activating the dose button to dispense the primary medicament from the first reservoir. Another preferred design would physically prevent insertion of the used drug dispense interface into the patient (e.g. a single use needle-guard type arrangement).

As mentioned a preferred design of our invention would include cartridges to contain the medicaments. The cartridge may be a multi dose cartridge having a piston and a pierceable septum. Cartridges are typically cylindrical in shape and are usually manufactured in glass, sealed at one end with a rubber bung (piston) and at the other end by a rubber septum using a metal ferrule. The dose delivery assemblies are typically powered by a manual action of the user, however, the injection mechanism may also be powered by other means such as a spring, compressed gas or electrical energy.

Exemplary embodiments of the present invention have been described. Those skilled in the art will understand, however, that changes and modifications may be made to these embodiments without departing from the true scope and spirit of the present invention, which is defined by the claims.

LIST OF REFERENCES 1 first medicament
2 second medicament
3 output needle
4 hub
5, 6 cartridge holder
7 rotational coupling
8, 9 dose delivery assembly
10 drug delivery device
12 dose setter
13 dose button

We claim:

1. A drug delivery device to deliver two or more medicaments operable through a single user-operable dose setter and a single dispense interface, comprising,
   a. a housing containing the user-operable dose setter operably connected to a first dose delivery assembly of a primary reservoir of a first medicament containing at least one dose of a drug agent;
   b. a dispense button operably connected to the primary reservoir of medicament;
   c. a single dispense interface configured for fluid communication with the primary reservoir; and
   d. a secondary reservoir of a second medicament containing at least one drug agent configured for fluid communication with the single dispense interface, wherein the user-operable dose setter is operably connected to a second dose delivery assembly of the second medicament;
   wherein a single activation of the dispense button causes the selected dose of the first medicament from the primary reservoir and the automatically set dose of the second medicament to be expelled through the single dispense interface,
   wherein the first and the second dose delivery assemblies are mechanically linked by a rotational coupling
   such that a rotation of the user-operable dose setter selects a dose of the primary medicament and automatically sets a non-user settable dose of the second medicament.

2. The device of claim 1 where a single operation of the dispense button causes the first and second medicaments to be expelled through the drug dispense interface simultaneously.

3. The device of claim 1, further comprising a first and a second dispense mechanism, wherein on activation of the dispense button the first dispense mechanism causes the dose of the first medicament to be forced through the dispense interface and the second dispense mechanism causes the dose of the second medicament to be forced through the dispense interface.

4. The device of claim 3, wherein each dispense mechanism comprises a lead screw acting on a bung in the reservoir.

5. The device of claim 1 where at least one of the primary and secondary reservoirs contains a liquid medicament.

6. The device of claim 1 where the single dispense interface is a hollow needle.

7. The device of claim 1 where the single dispense interface is a system of hollow needle cannulae in fluid communication with the primary and secondary reservoirs.

8. The device of claim 1 where at least one of the primary reservoir and the secondary reservoir is replaceable.

9. The device of claim 1 where at least one of the primary reservoir and the secondary reservoir is fixed in a reservoir holder and is not replaceable.

10. The device of claim 1 where the primary reservoir is replaceable and the secondary reservoir is fixed in a reservoir holder and is not replaceable.

11. The device of claim 1 where at least one of the primary reservoir and the secondary reservoir comprises multiple doses of a medicament.

12. A method of dispensing a user settable dose of a first medicament and a dose of a second medicament from separate reservoirs, comprising, in combination, the steps of
   a. setting a dose of the first medicament contained in a primary reservoir by rotation of a dose setter of a drug delivery device;

b. automatically setting a non-user settable dose of a second medicament in a secondary reservoir based on the set dose of the first medicament via a rotational coupling;

c. activating a dispense button to move the set dose of the first medicament and the automatically set dose of the second medicament from the primary and secondary reservoirs in a distal direction; and d. forcing the set dose of the first medicament and the automatically set dose of the second medicament through a single drug dispense interface.

13. The method of claim 12 wherein the second medicament is forced through the single dispense interface simultaneously with the flow of the first medicament.

14. The device of claim 1, where the rotational coupling is configured in such a manner that upon rotation of the single user-operable dose setter the first and the second dose delivery assemblies rotate in the same direction.

* * * * *